United States Patent
Murashima et al.

(10) Patent No.: US 10,408,715 B2
(45) Date of Patent: Sep. 10, 2019

(54) ADSORPTION PUMP

(71) Applicant: Panasonic Corporation, Osaka (JP)

(72) Inventors: Yuji Murashima, Osaka (JP); Masaya Nakatani, Hyogo (JP); Atsuo Nakao, Nara (JP)

(73) Assignee: PANASONIC CORPORATION, Osaka (JP)

( * ) Notice: Subject to any disclaimer, the term of this patent is extended or adjusted under 35 U.S.C. 154(b) by 50 days.

(21) Appl. No.: 15/554,225

(22) PCT Filed: Mar. 25, 2016

(86) PCT No.: PCT/JP2016/001730
§ 371 (c)(1),
(2) Date: Aug. 29, 2017

(87) PCT Pub. No.: WO2016/174814
PCT Pub. Date: Nov. 3, 2016

(65) Prior Publication Data
US 2018/0038776 A1  Feb. 8, 2018

(30) Foreign Application Priority Data
Apr. 28, 2015 (JP) .................... 2015-091929

(51) Int. Cl.
*G01N 1/22* (2006.01)
*G01N 1/40* (2006.01)
(Continued)

(52) U.S. Cl.
CPC ........... *G01N 1/2214* (2013.01); *G01N 1/405* (2013.01); *G01N 30/08* (2013.01); *G01N 30/80* (2013.01);
(Continued)

(58) Field of Classification Search
CPC ......... G01N 1/2214; G01N 2001/2217; G01N 1/405; G01N 30/08; G01N 2030/085;
(Continued)

(56) References Cited

U.S. PATENT DOCUMENTS

| | | | |
|---|---|---|---|
| 5,861,053 A | 1/1999 | Noritake et al. | |
| 8,702,930 B2 * | 4/2014 | Hashimotodani | G01N 33/48728 204/400 |

(Continued)

FOREIGN PATENT DOCUMENTS

| | | |
|---|---|---|
| EP | 2045593 A2 | 4/2009 |
| GB | 2434643 A | 8/2007 |

(Continued)

OTHER PUBLICATIONS

The Extended European Search Report dated Apr. 11, 2018 for the related European Patent Application No. 16786096.4.
(Continued)

*Primary Examiner* — Robert R Raevis
(74) *Attorney, Agent, or Firm* — McDermott Will & Emery LLP (57) ABSTRACT

An adsorption pump includes a housing, a movable part, and an adsorption part. The housing has inlet and outlet ports for a sample. The movable part is at least partly located inside the housing. The adsorption part is located inside the housing.

10 Claims, 5 Drawing Sheets

(51) Int. Cl.
*G01N 30/08* (2006.01)
*G01N 30/80* (2006.01)
*G01N 1/24* (2006.01)
*G01N 30/84* (2006.01)

(52) U.S. Cl.
CPC ..... *G01N 1/2273* (2013.01); *G01N 2001/245* (2013.01); *G01N 2030/8411* (2013.01); *G01N 2030/8417* (2013.01)

(58) Field of Classification Search
CPC ...... G01N 30/80; G01N 30/82; G01N 1/2273; G01N 1/24; G01N 2001/245; G01N 2030/8411; G01N 2030/8417
USPC ... 73/863.12, 31.07, 863.21, 864.34, 864.35; 417/63; 422/83, 88–92
See application file for complete search history.

(56) References Cited

U.S. PATENT DOCUMENTS

| | | | |
|---|---|---|---|
| 2004/0007048 A1* | 1/2004 | Rabenecker | G01N 1/24 73/23.2 |
| 2008/0007728 A1* | 1/2008 | Schneider | G01N 1/2273 356/301 |
| 2008/0078256 A1* | 4/2008 | Christie | B01L 3/502 73/863.23 |
| 2012/0132798 A1 | 5/2012 | Cambron et al. | |
| 2013/0309108 A1* | 11/2013 | Haeberer | F04B 17/04 417/413.1 |
| 2013/0312490 A1 | 11/2013 | Verdier et al. | |

FOREIGN PATENT DOCUMENTS

| | | | |
|---|---|---|---|
| JP | 9-057061 | | 3/1997 |
| JP | 9-196830 | | 7/1997 |
| JP | 2007152826 | * | 6/2007 |
| JP | 2012-026954 | | 2/2012 |
| JP | 2012-220454 | | 11/2012 |
| JP | 2013-037213 | | 2/2013 |
| JP | 2013-541016 | | 11/2013 |
| JP | 2014-014760 | | 1/2014 |

OTHER PUBLICATIONS

International Search Report of PCT application No. PCT/JP2016/001730 dated Jun. 14, 2016.

* cited by examiner

ADSORPTION PUMP

This application is a U.S. national stage application of the PCT international application No. PCT/JP2016/001730 filed on Mar. 25, 2016, which claims the benefit of foreign priority of Japanese patent application No. 2015-091929 filed on Apr. 28, 2015, the contents all of which are incorporated herein by reference.

TECHNICAL FIELD

The present disclosure relates to an adsorption pump capable of adsorbing volatile organic compounds contained in a sample.

BACKGROUND ART

Exhaust gas, air, and exhaled breath contain volatile organic compounds (VOC). It has been known to that volatile organic compounds contained in a sample can be separated, concentrated, recovered, and detected by an adsorption method.

PTL 1 discloses a device including an adsorption tower filled with an adsorbent for adsorbing VOC, and a pump for feeding a sample into the tower. PTL 2 discloses a device including an adsorption part onto which gas is adsorbed, and a pump for compressing the gas and then feeding the compressed gas to the adsorption part.

CITATION LIST

Patent Literature

PTL 1: Japanese Patent Laid-Open Publication No. 2014-14760
PTL 2: Japanese Patent Laid-Open Publication No. 2012-220454

SUMMARY

The present disclosure provides an adsorption pump reduces a size of a device on which the adsorption pump is mounted.

The adsorption pump according to the present disclosure includes a housing, a movable part, and an adsorption part. The housing has inlet and outlet ports for a sample. The movable part is at least partly located inside the housing. The adsorption part is located inside the housing.

The adsorption pump according to the present disclosure reduces a size of a device on which the adsorption pump is mounted.

DETAIL DESCRIPTION OF PREFERRED EMBODIMENTS

Prior to describing exemplary embodiments of the present invention, problems of conventional devices will be described below. A conventional device includes a pump and an adsorption part as separate components, hardly having a small size.

The adsorption pump according to exemplary embodiments of the present disclosure will be detailed below with reference to the accompanying drawings. These exemplary embodiments are examples of the present disclosure. The numerical values, the shapes, the materials, the components, and the layout and connection of the components shown in these embodiments are mere examples and do not intend to limit the present disclosure.

The drawings are schematic and not to scale. In the drawings, approximately the same components are denoted by the same reference numerals, and a description of the same components as those in preceding embodiments will be omitted or simplified.

Exemplary Embodiment 1

Figure 1:
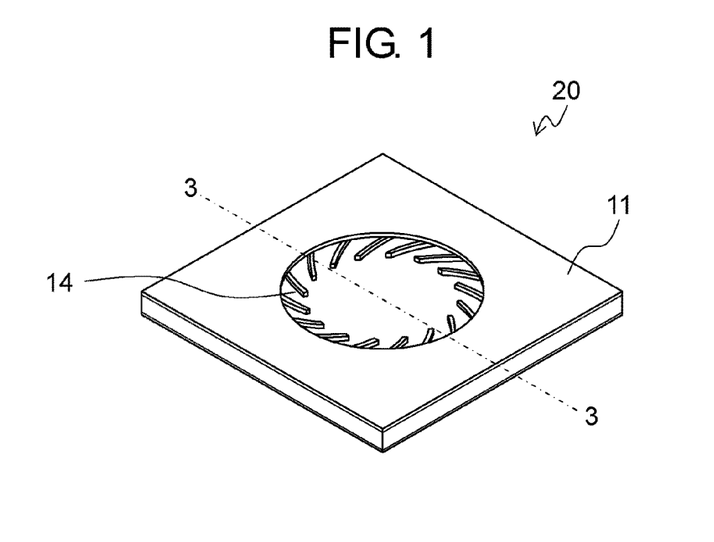
FIG. 1 is a schematic perspective view of an adsorption pump according to Exemplary Embodiment 1 of the present disclosure.
Figure 2:
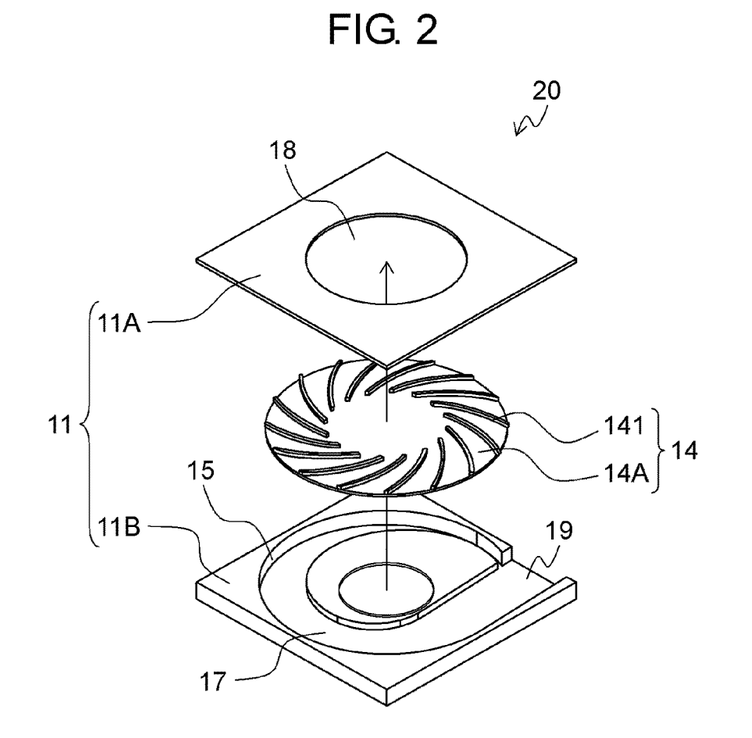
FIG. 2 is a schematic exploded perspective view of the adsorption pump shown in FIG. 1.
Figure 3:
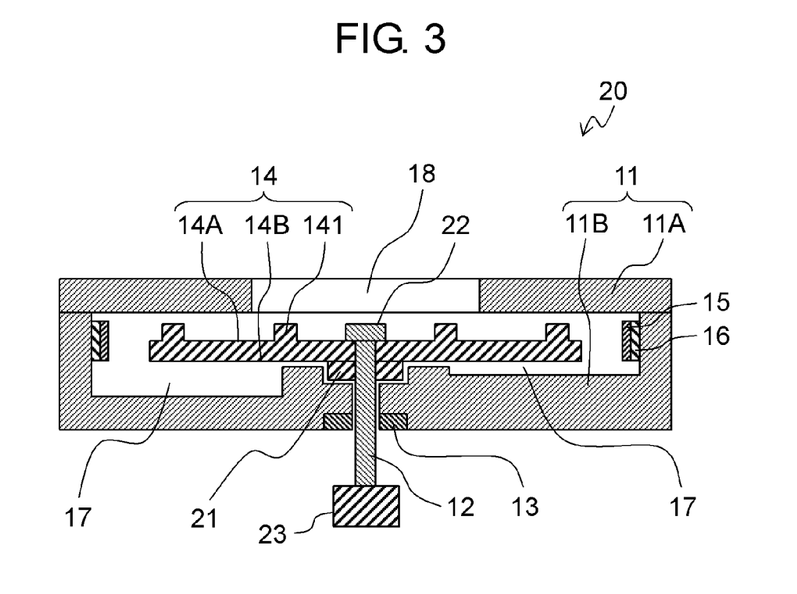
FIG. 3 is a schematic sectional view of the adsorption pump shown in FIG. 1.

FIG. 1 is a schematic perspective view of centrifugal adsorption pump 20 according to Exemplary Embodiment 1 of the present disclosure. FIG. 2 is a schematic exploded perspective view of adsorption pump 20. FIG. 3 is a schematic sectional view of adsorption pump 20 along line 3-3 shown in FIG. 1.

Adsorption pump 20 is a centrifugal pump called a turbo pump with backward blades.

Adsorption pump 20 can transport a sample containing a specific chemical substance and adsorb the specific chemical substance. The chemical substance is, for example, a volatile organic compound (VOC).

As shown in FIGS. 2 and 3, adsorption pump 20 includes housing 11, main shaft 12, bearing 13, impeller 14, adsorption part 15, and heating part 16.

As shown in FIG. 2, housing 11 includes upper housing 11A and lower housing 11B. Spiral scroll 17 is provided in housing 11. Scroll 17 is an inward scroll located under impeller 14 inside adsorption pump 20. This configuration provides adsorption pump 20 with a small size. Housing 11 has inlet port 18 through which a sample is brought into housing 11, and has outlet port 19 through which the sample is discharged outside housing 11. The center of inlet port 18 coincides with the axis of rotation of impeller 14. Outlet port 19 is communicated with scroll 17. A cross sectional area of a portion of scroll 17 increases as the portion of scroll 17 approaches outlet port 19.

Impeller 14 is a rotor with blades 141. As shown in FIG. 3, impeller 14 has blade surface 14A having blades 141 thereon and rear surface 14B opposite to blade surface 14A. Blade surface 14A faces inlet port 18. Impeller 14 located inside housing 11 is a movable part of adsorption pump 20. Rear surface 14B of impeller 14 includes boss 21 to maintain a constant distance between housing 11 and rear surface 14B. Housing 11 also has a recess therein to accommodate boss 21.

Main shaft 12 penetrates housing 11 (lower housing 11B), and is rotatable with respect to housing 11. Main shaft 12 has a first end fixed to impeller 14 with screw 22, and has a second end coupled to driver 23 located outside housing 11. Driver 23 is, for example, a motor. Screw 22 is unnecessary if impeller 14 and main shaft 12 are unitarily molded. Impeller 14 converts the rotational energy of driver 23 into kinetic energy.

Bearing 13 supports main shaft 12, and is, for example, a ball bearing or a hydrodynamic air bearing, and is located in housing 11. Hydrodynamic air bearings are used for low-load high-speed conditions. The type of bearing 13 is determined depending on the rotation speed of impeller 14 and a load on impeller 14.

Adsorption part 15 adsorbs chemical substances contained in a sample. Chemical substances are selectively adsorbed on different adsorbents. Adsorption part 15 is located inside housing 11. Adsorption pump 20 provides, for example, a chemical substance detection device, with a small size. Adsorption part 15 is formed, for example, on a side surface of scroll 17. The sample discharged through the exit of impeller 14 hits the side surface of scroll 17.

Heating part 16 for heating adsorption part 15 is located near adsorption part 15 so as to efficiently heat adsorption part 15.

Figure 4:
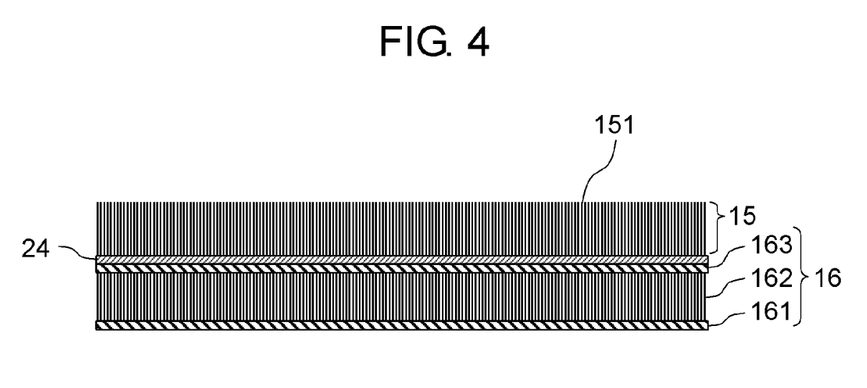
FIG. 4 is an enlarged schematic view of an adsorption part and a heating part of the adsorption pump shown in FIG. 3.

FIG. 4 is an enlarged schematic view of adsorption part 15 and heating part 16. Adsorption part 15 includes nanofibers 151. Heating part 16 is located under adsorption part 15.

As described later, nanofibers 151 may be located on a seed layer. The seed layer is, for example, a material layer or catalyst layer of nanofibers 151.

Nanofibers 151 are coated with an adsorbent that selectively adsorbs a chemical substance. For example, in order to selectively adsorb carbon monoxide, the adsorbent can be nickel or silver. In order to selectively adsorb ammonia or chlorine, the adsorbent can be molybdenum. In order to selectively adsorb nitrogen oxide, the adsorbent can be zeolite. In order to selectively adsorb hydrogen, the adsorbent can be palladium. In order to selectively adsorb water, the adsorbent can be polyaniline Thus, the adsorbent can be selected depending on the VOC to be adsorbed. Nanofibers 151 may alternatively be made of an adsorbent that selectively adsorbs a specified chemical substance.

Heating part 16 includes lower electrode 161, upper electrode 163, and nanofibers 162 provided between lower electrode 161 and upper electrode 163. Nanofibers 162 are conductive and electrically coupled to lower electrode 161 and upper electrode 163, which are a first electrode and a second electrode, respectively. Lower electrode 161 and upper electrode 163 are coupled to a power supply located inside or outside housing 11.

Upon having a current flowing each nanofiber 162, nanofibers 162 generate heat due to their resistance. This property allows nanofibers 162 to be used as heating part 16.

Heating part 16 containing nanofibers 162 can be heated with low power, and can heat adsorption part 15 efficiently at low power accordingly. Nanofibers 162 have a small heat capacity, so that heating part 16 is cooled rapidly. Therefore, heating part 16 containing nanofibers 162 can heat or cool adsorption part 15 rapidly.

Nanofibers 151 and 162 may be made of either the same material or different materials.

Figure 5:
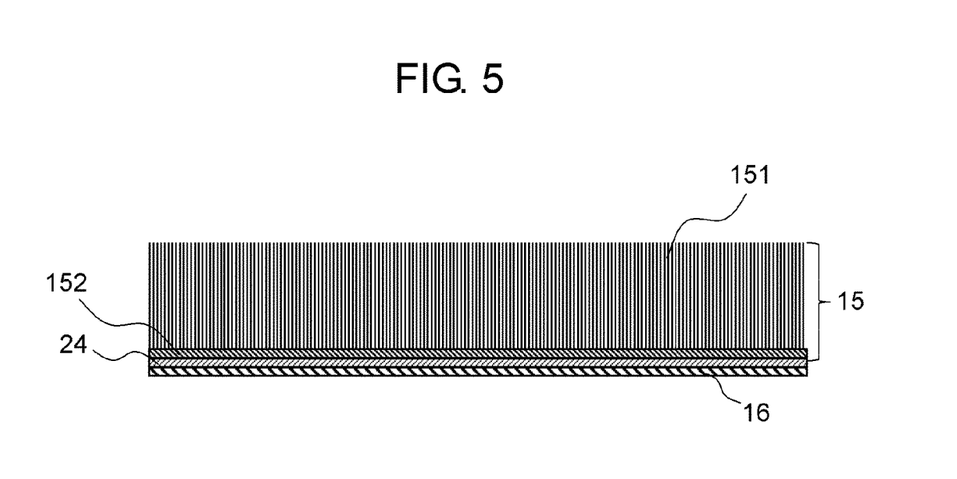
FIG. 5 is an enlarged schematic view of another adsorption part and another heating part of the adsorption pump shown in FIG. 3.

Heating part 16 may be made of a metal wiring pattern or a wiring pattern of resistance heating material, as shown in FIG. 5. Alternatively, heating part 16 may be a meandering NiCr thin film.

In FIG. 5, nanofibers 151 are located on seed layer 152. Nanofibers 151 have a small heat capacity due to their structure, and can heat adsorption part 15 efficiently at low power. Nanofibers 151 also increase the speed at which adsorption part 15 is cooled. Heating part 16 is coupled to the power supply located inside or outside housing 11.

Insulating layer 24 may be provided between adsorption part 15 and heating part 16. In this case, the current supplied to heating part 16 does not flow to adsorption part 15, so that heating part 16 can heat adsorption part 15 efficiently.

An operation of adsorption pump 20 will be described below. Impeller 14 rotates in response to a rotation of driver 23. The rotation of impeller 14 reduces a pressure at a region in housing 11 near the axis of the rotation while increasing a pressure at a region in housing 11 between blades 141. The sample flows into the region near the axis of rotation of impeller 14, then receives a kinetic energy due to a centrifugal force of impeller 14, and is carried to the exit of impeller 14. After that, the sample is recovered from dynamic to static pressure in scroll 17 in housing 11. The sample discharged through the exit of impeller 14 is efficiently collected by scroll 17 and exhausted through outlet port 19.

At this moment, the sample contacts adsorption part 15 on the side surface of scroll 17, and allows chemical substances contained in the sample to be efficiently adsorbed onto adsorption part 15. After that, adsorption part 15 is heated by heating part 16. The chemical substances adsorbed on adsorption part 15 are removed from adsorption part 15 due to the heating. Consequently, adsorption pump 20 can exhaust the chemical substances concentrated on adsorption part 15. Adsorption part 15 recovers its adsorption function when the chemical substances are removed from adsorption part 15.

If adsorption pump 20 has enough space, or impeller 14 has a high circumferential speed, adsorption pump 20 may include a diffuser. The diffuser is located, for example, on a bottom surface of lower housing 11B so as to efficiently recover the kinetic energy of gas molecules in the form of pressure. Adsorption pump 20 including the diffuser can efficiently recover the kinetic energy of gas molecules in the form of static pressure. In this case, scroll 17 can be an outward spiral scroll.

Adsorption pump 20 may have a Sirocco fan with forward blades or a fan with radial blades.

Figure 6:
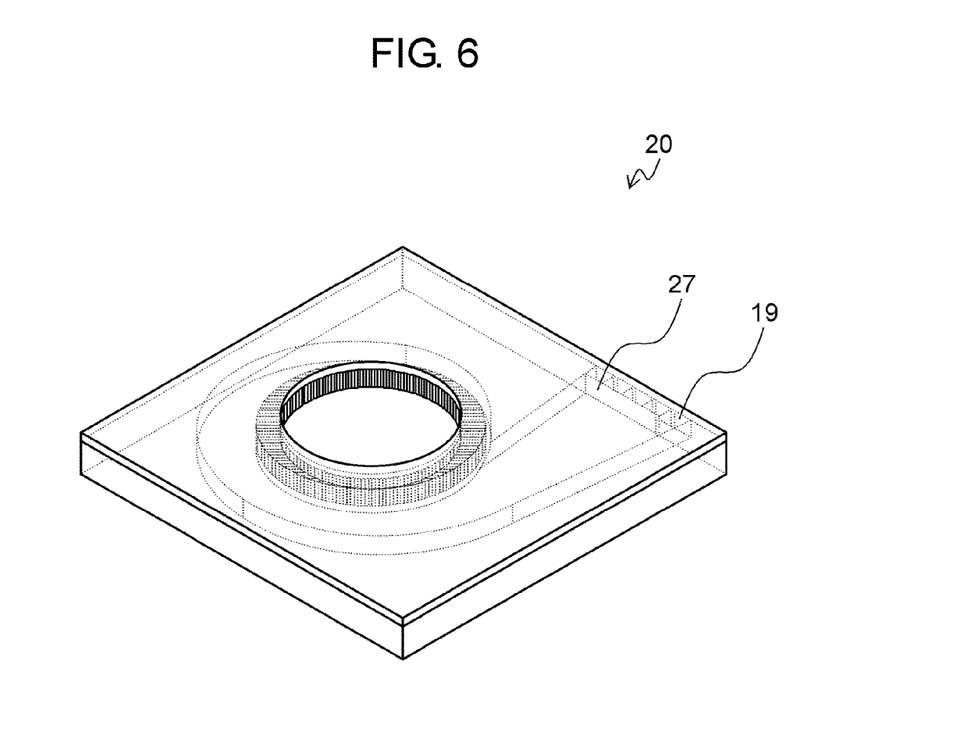
FIG. 6 is a schematic perspective view of another adsorption pump according to Embodiment 1 of the present disclosure.

Outlet port 19 of adsorption pump 20 may be divided into ports, as shown in FIG. 6. Outlet ports 19 may be partitioned by partition board 27 or other similar device. The position of partition board 27 can be changed depending on whether adsorption part 15 is being heated or not. As a result, a part of the sample that contains a lot of the adsorbed chemical substances and the remaining part of the sample that contains fewer adsorbed chemical substances are flow through different passages.

Figure 7:
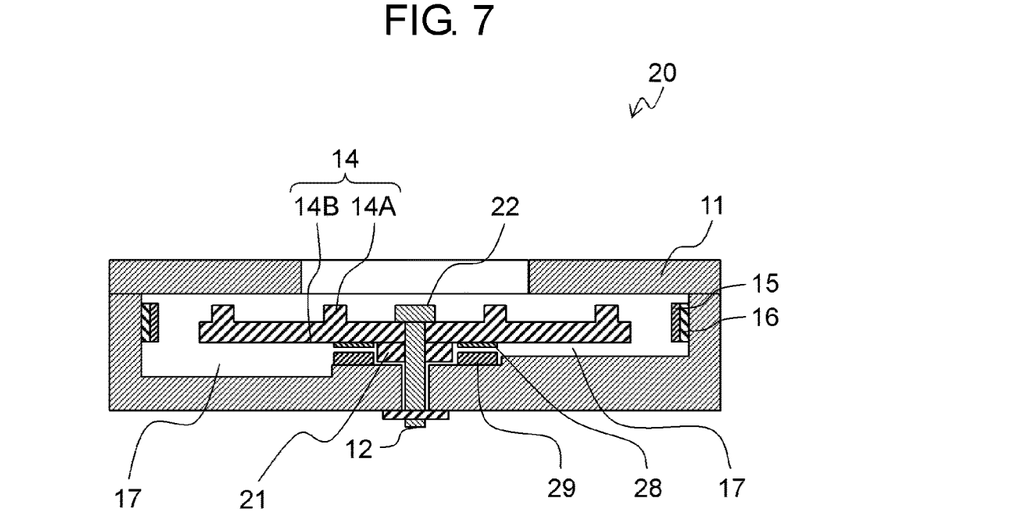
FIG. 7 is a schematic sectional view of the adsorption pump shown in FIG. 6.

Driver 23 may be located inside housing 11, as shown in FIG. 7. For example, rotor 28 may be located on rear surface 14B of impeller 14 and stator 29 on the inner wall of housing 11 facing rotor 28. Stator 29 is, for example, an air-core coil while rotor 28 is, for example, a magnet. A current applied to stator 29 to generate a magnetic force driving rotor 28. The force applied to rotor 28 rotates impeller 14.

Adsorption part 15 is located on the side surface of scroll 17 so as to efficiently adsorb the chemical substances, but this location is not the only option available. For example, adsorption part 15 may alternatively be located on an upper surface or a lower surface of scroll 17. In either configuration, adsorption part 15 can adsorb chemical substances. In the case that adsorption part 15 is located on the lower surface of scroll 17, adsorption part 15 can be formed by bottom-up or top-down process in MEMS process. This process simplifies the manufacture of adsorption pump 20.

Modified Example 1

Modified example 1 according to the embodiment will be described below.

Figure 8:
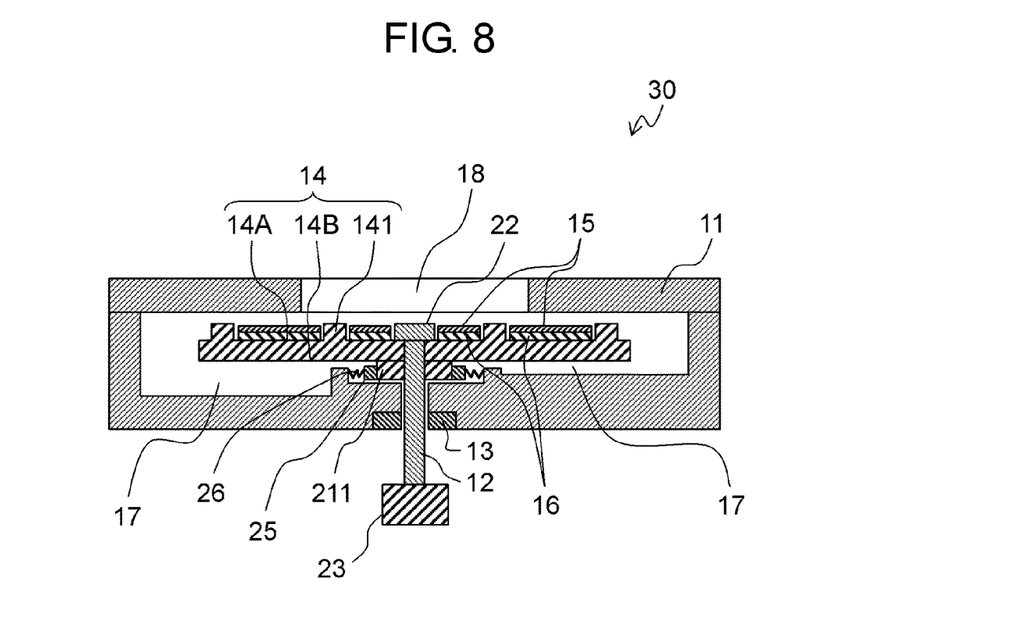
FIG. 8 is a schematic sectional view of an adsorption pump according to modified example 1 different from Embodiment 1 of the present disclosure.

FIG. 8 is a schematic perspective view of adsorption pump 30 of modified example 1 according to the present embodiment.

Adsorption pump 30 is different from Embodiment 1 in that adsorption part 15 and heating part 16 are located on blade surface 14A of impeller 14. The other structures and operations are identical to those of Embodiment 1. Therefore, the same components as in Embodiment 1 are denoted by the same reference numerals, and their description will be omitted.

Adsorption part 15 is located on the suction surface of blade surface 14A of impeller 14. The suction surface is a surface between blades 141 into which a flow velocity vector of the sample is directed while impeller 14 rotates. Since the sample flows onto the suction surface, the chemical substances are efficiently adsorbed onto adsorption part 15.

Adsorption part 15 is preferably located in a region facing inlet port 18 so as to firmly adsorb the chemical substances contained in the sample.

Rear surface 14B of impeller 14 includes boss 211 for maintaining a constant distance between housing 11 and the rear surface. Boss 211 is electrically coupled to heating part 16. Boss 211 contacts conductive brush 25 in the recess of housing 11. Conductive brush 25 is electrically coupled to an external power supply via spring 26. Brush 25 continuously contact boss 211 by a constant force of spring 26, so that the rotational load of impeller 14 is within an appropriate range of torque of driver 23. A current is applied to heating part 16 current via conductive brush 25 and spring 26.

In adsorption pump 30, heating part 16 may be located on an inner wall of housing 11 facing adsorption part 15. In this case, adsorption part 15 is heated by radiant heat from heating part 16. In this structure, the chemical substances can be removed from adsorption part 15. Heating part 16 in housing 11, which is a fixed part, allows wiring for applying a current to heating part 16 to be arranged easily.

The chemical substances can alternatively be removed by vibration. In this case, a vibrator can be used as a removal mechanism instead of heating part 16. The vibrator is, for example, a piezoelectric element including upper and lower electrodes and a piezoelectric material sandwiched between the upper and lower electrodes.

The chemical substances can alternatively be removed by light. In this case, a light source can be located, as the removal mechanism, in a region inside housing 11 facing adsorption part 15.

The removal mechanism, such as heating part 16, is unnecessary in some applications of the adsorption pump.

As described above, adsorption part 15 is located on blade surface 14A of impeller 14, which is the movable part. Therefore, the movable part also functions as a vibrator. The rotation of the movable part allows the chemical substances adsorbed on adsorption part 15 to be removed efficiently.

Exemplary Embodiment 2

Figure 9:
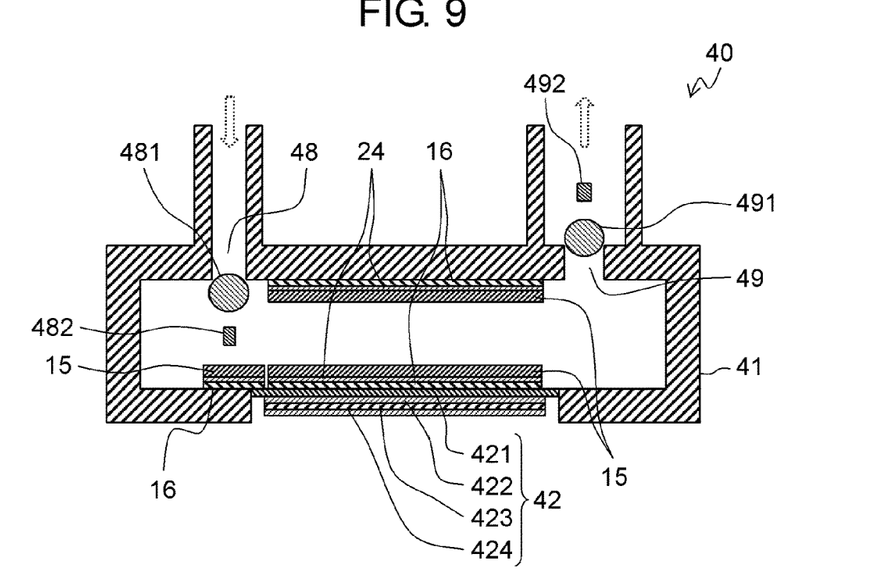
FIG. 9 is a schematic sectional view of an adsorption pump according to Exemplary Embodiment 2 of the present disclosure.

FIG. 9 is a schematic sectional view of diaphragm adsorption pump 40 according to Exemplary Embodiment 2 of the present disclosure. Adsorption pump 40 can transport a sample containing a chemical substance and adsorb the chemical substance. The chemical substance is, for example, volatile organic compound (VOC).

Adsorption pump 40 includes housing 41, diaphragm 42 for changing the volume of housing 41, adsorption part 15, and heating part 16.

Housing 41 has inlet port 48 through which the sample is introduced into housing 41, and outlet port 49 through which the sample is discharged outside housing 41. Check valve 481 for preventing the backflow of the sample is provided at inlet port 48. Housing 41 further includes stopper 482 facing check valve 481 so as to control an operation of valve 481. Check valve 491 for preventing the backflow of the sample is provided at outlet port 49. Housing 41 further includes stopper 492 facing check valve 491 so as to control an operation of valve 491.

Diaphragm 42 has a bimorph structure including, for example, vibration plate 421, upper electrode 422, piezoelectric element 423, and lower electrode 424 which are stacked on one another. Piezoelectric element 423 is made of, for example, $Pb(Zr,Ti)O_3$, which is hereinafter referred to as PZT. In diaphragm 42, vibration plate 421, upper electrode 422, piezoelectric element 423, and lower electrode 424 are stacked in this order from inside to outside of housing 41. Diaphragm 42 is a movable part of adsorption pump 40 and is partly located inside housing 41. The phrase "is partly located inside the housing" includes the case of being partly located as part of the wall of housing 41.

Adsorption pump 40 is driven by piezoelectric element 423 used as a component of diaphragm 42. The piezoelectric element advantageously provides adsorption pump 40 with a small size and small power consumption, but this is not the only option available. For example, diaphragm 42 may be driven by an electromagnetic field generated by either a magnet or a magnetostrictive material and a coil, or may be driven by an electrostatic force. Alternatively, diaphragm 42 may be driven by a DC motor.

Adsorption part 15 and heating part 16 are located on diaphragm 42 and a portion of the inner wall of housing 41 facing diaphragm 42. Thus, adsorption part 15 is located inside housing 11, so that adsorption pump 40 reduces a size of a chemical substance detection device or other similar device on which adsorption pump 40 is mounted. Heating part 16 is located near adsorption part 15 and therefore can heat adsorption part 15 efficiently.

Adsorption part 15 is provided on the heating part 16 provided on diaphragm 42 while adsorption part 15 is provided on heating part 16 provided on the inner wall of housing 41.

Adsorption part 15 includes, for example, nanofibers 151 and seed layer 152, as shown in FIG. 5. Insulating layer 24 is provided between adsorption part 15 and heating part 16.

Adsorption part 15 is not necessarily located on diaphragm 42 as long as adsorption part 15 is located inside housing 41. For example, adsorption part 15 may be located on a region of the inner wall of housing 41 facing inlet port

48. In this case, adsorption part 15 can firmly adsorb chemical substances contained in the sample.

An operation of adsorption pump 40 will be described below. Upon having an alternating-current (AC) voltage having a frequency identical to the resonance frequency of diaphragm 42 applied to piezoelectric element 423, diaphragm 42 deforms. This deformation of diaphragm 42 changes the volume of housing 41.

When the volume increases, housing 41 has a negative pressure therein, so that check valve 481 opens while check valve 491 is closed simultaneously, thereby introducing the sample into housing 41. When the volume decreases, housing 41 has a positive pressure, so that check valve 481 is closed while check valve 491 opens simultaneously, thereby exhausting the sample outside housing 41. The volume of housing 41 alternately increases and decreases as described above, adsorption pump 40 causes the sample to flow in a single direction.

At this moment, the sample contacts adsorption part 15 located inside housing 41. As a result, the chemical substances contained in the sample are efficiently adsorbed onto adsorption part 15. After that, adsorption part 15 is heated by thermal conduction or radiant heat from heating part 16. The chemical substances adsorbed on adsorption part 15 are removed from adsorption part 15 by the heating. Consequently, adsorption pump 40 can exhaust the chemical substances concentrated on adsorption part 15. Adsorption part 15 recovers its adsorption function when the chemical substances are removed from adsorption part 15.

Outlet port 49 of adsorption pump 40 may be divided into plural ports, similarly the pump according to Embodiment 1 shown in FIG. 6. These outlet ports may be partitioned by a partition board or other similar device.

As described above, adsorption part 15 is located in housings 11 and 41 in adsorption pumps 20 and 30, respectively. Adsorption pump 20 and 30 reduce a size of a chemical substance detection device or other similar device on which they are mounted.

A temperature at which the chemical substances are removed is different depending on the type of the substances. Therefore, the substances adsorbed on adsorption part 15 can be removed by controlling the value and time period of a current applied to heating part 16 depending on the type of the substances.

Alternatively, plural adsorption parts 15 made of different adsorbents may be located inside housings 11 and 41. In adsorption pump 20, plural adsorption parts 15 are separately placed between blades 141 of impeller 14. In this case, different types of chemical substances can be separately adsorbed in adsorption pumps 20 and 30. The adsorption part 15 onto which a specific chemical substance has been adsorbed may be selectively heated to remove this specific substance alone.

Figure 10:
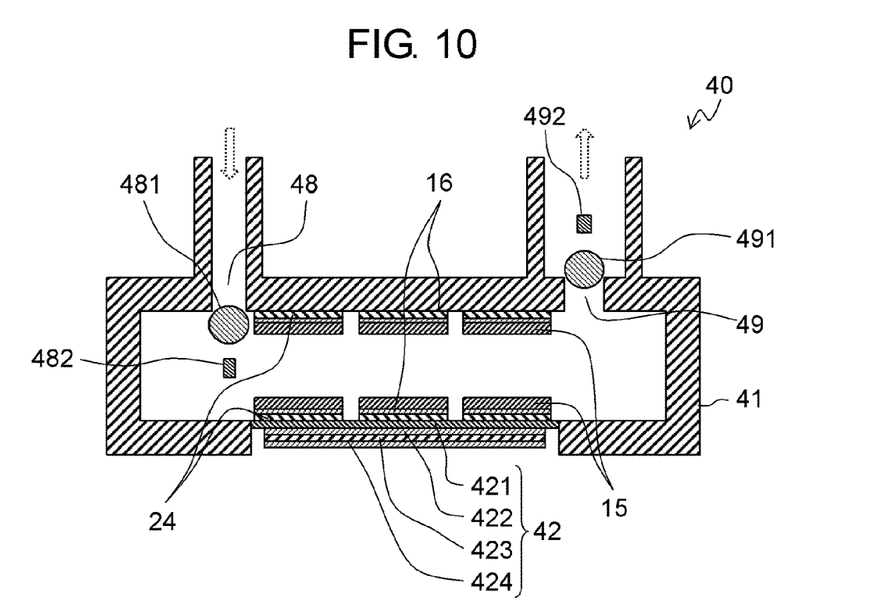
FIG. 10 is a schematic sectional view of another adsorption pump according to Embodiment 2 of the present disclosure.

As another example, as shown in FIG. 10, adsorption pump 40 includes plural adsorption parts 15 made of different adsorbents. In this case, plural heating parts 16 are formed to correspond to the adsorption parts 15. Heating parts 16 can be heated separately. Adsorption pump 40 with this configuration provides similar effects.

The adsorbent as a component of adsorption part 15 does not necessarily include nanofibers 151, and may alternatively be, for example, a porous body.

Heating part 16 may be replaced by a vibrator. The vibrator vibrates adsorption part 15 to remove the chemical substances adsorbed on adsorption part 15. Thus, heating part 16 and the vibrator function as a removal part for removing the adsorbed chemical substances from adsorption part 15. However, the removal part is unnecessary in some applications of the adsorption pump.

An electrode may be coupled to nanofibers 151 of adsorption part 15 and a current may be applied to the electrode. In this case, adsorption part 15 per se functions as heating part 16.

The different types of adsorption pumps have been described in the exemplary embodiments, but the present disclosure is not limited to these exemplary embodiments. Various modifications designed by a person having ordinary skill in the art, or a combination of components of different embodiments may be included in one or more exemplary embodiments as long as they do not greatly deviate from the spirit of the present disclosure.

INDUSTRIAL APPLICABILITY

An adsorption pump according to the present disclosure is useful in devices for transporting a sample containing chemical substance and adsorbing the substance.

REFERENCE MARKS IN THE DRAWINGS

11, 41 housing
11A upper housing
11B lower housing
12 main shaft
13 bearing
14 impeller
141 blade
14A blade surface
14B rear surface
15 adsorption part
151 nanofiber
152 seed layer
16 heating part
161 lower electrode
162 nanofiber
163 upper electrode
17 scroll
18, 48 inlet port
19, 49 outlet port
20, 30, 40 adsorption pump
21, 211 boss
22 screw
23 driver
24 insulating layer
25 conductive brush
26 spring
27 partition board
28 rotor
29 stator
42 diaphragm
421 vibration plate
422 upper electrode
423 piezoelectric element
424 lower electrode
481, 491 check valve
482, 492 stopper

The invention claimed is:
1. An adsorption pump comprising:
a housing having an inlet port and an outlet port for a sample;
a movable part at least partly located inside the housing; and
an adsorption part located inside the housing;

wherein the absorption part is located in the movable part, and wherein the movable part includes an impeller including a blade.

2. The adsorption pump according to claim 1, wherein the adsorption part comprises nanofibers.

3. The adsorption pump according to claim 2, wherein the adsorption part is located in a region facing the inlet port.

4. The adsorption pump according to claim 2, further comprising a removal part configured to remove, from the adsorption part, a chemical substance adsorbed on the adsorption part.

5. The adsorption pump according to claim 4, wherein the removal part comprises a heating part configured to heat the adsorption part.

6. The adsorption pump according to claim 5, wherein the heating part includes:
   a first electrode;
   a second electrode; and
   conductive nanofibers electrically coupled to each of the first electrode and the second electrode.

7. The adsorption pump according to claim 5, wherein the heating part is made of a conductive thin film having a meandering shape.

8. The adsorption pump according to claim 1, wherein the adsorption part is fixed to the impeller.

9. The adsorption pump according to claim 8,
   wherein the impeller has a blade surface from which the blade projects, and
   wherein the adsorption part is fixed to the blade surface of the impeller.

10. The adsorption pump according to claim 8,
    wherein the impeller includes a plurality of blades including the blade,
    wherein the impeller has a blade surface from which the plurality of blades projects, and
    wherein the adsorption part is fixed to the blade surface of the impeller surface between the plurality of blades.

* * * * *